US00PP27317P3

(12) United States Plant Patent
Meilland

(10) Patent No.: US PP27,317 P3
(45) Date of Patent: Nov. 1, 2016

(54) FLORIBUNDA ROSE PLANT NAMED 'MEIPLUMTY'

(50) Latin Name: *Rosa hybrida*
Varietal Denomination: Meiplumty

(71) Applicant: CP DELAWARE, INC., Wilmington, DE (US)

(72) Inventor: Alain M. Meilland, Antibes (FR)

(73) Assignee: CP Delaware, Inc, Wilmington, DE (US)

( * ) Notice: Subject to any disclaimer, the term of this patent is extended or adjusted under 35 U.S.C. 154(b) by 31 days.

(21) Appl. No.: 14/121,068

(22) Filed: Jul. 28, 2014

(65) Prior Publication Data

US 2016/0029526 P1 Jan. 28, 2016

(51) Int. Cl.
*A01H 5/02* (2006.01)

(52) U.S. Cl.
USPC ..... Plt./148

(58) Field of Classification Search
USPC ..... Plt./103, 107, 144, 148
See application file for complete search history.

(56) References Cited

PUBLICATIONS

Star Roses & Plants. Look-A-Likes Apple Dapple, Rosa 'Meiplumty', retrieved on Jan. 7, 2016, retrieved from the Internet at <http://www.starrosesandplants.com/plants/landscape-shrub-rose/look-likes-apple-dapple> 4pp.*

Michigan Bulb Co. Apple Dapple Groundcover Rose, retrieved on Jan. 7, 2016, retrieved from the Internet at <http://www.michiganbulb.com/product/apple-dapple-groundcover-rose/New_Garden_Plants> 2 pp.*

* cited by examiner

*Primary Examiner* — June Hwu
(74) *Attorney, Agent, or Firm* — Buchanan Ingersoll & Rooney PC

(57) ABSTRACT

A new and distinct Floribunda rose plant is provided that commonly commences blooming medium in the season and forms abundantly and nearly continuously in mass attractive single light pink blossoms. The growth habit is low, compact, and bushy. Strong vegetation is formed. The vegetation is dense and bears a glossy aspect on the upper surface. Good tolerance to disease has been observed particularly with respect to black spot and mildew. The plant is well suited for providing attractive ornamentation in parks and gardens.

1 Drawing Sheet

Figures 1, 2, 3, 4, 5, 6, 7, 8, 9, 10, 11, 12, 13, 14:
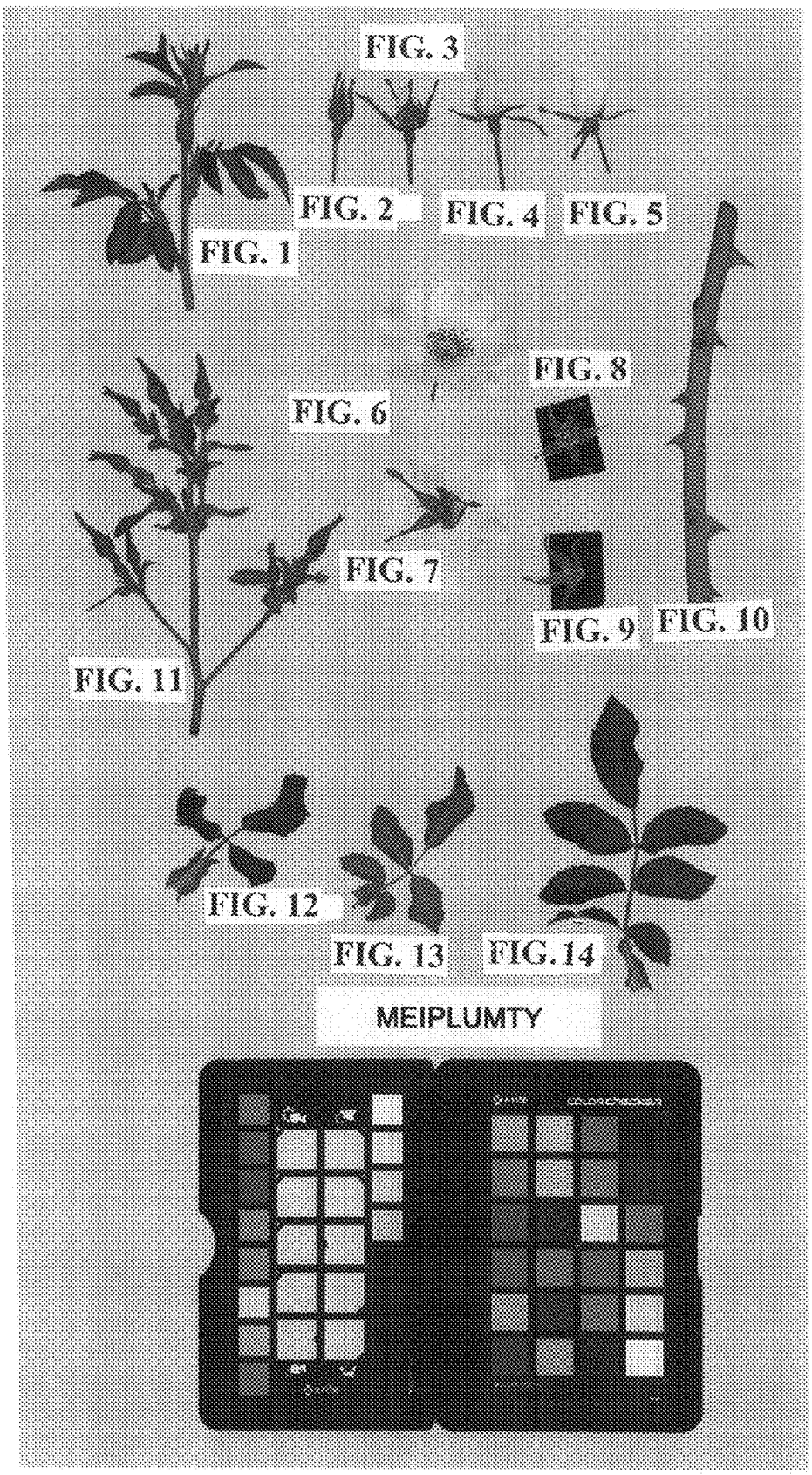

Botanical/commercial classification: *Rosa hybrida*/Floribunda Rose Plant.

Varietal denomination: cv. Meiplumty.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) was the 'Noacas' variety (non-patented in the United States). The male parent (i.e., the pollen parent) was an unnamed and unreleased seedling (non-patented in the United States).

The parentage of the new variety can be summarized as follows:

'Noacas'×'Unnamed Seedling'.

The seeds resulting from the above pollination were sown and small plants were obtained which were physically and biologically different from each other. Selective study resulted in the identification of a single plant of the new variety.

It was found that the new Floribunda rose plant of the present invention:

(a) displays a low and compact bushy growth habit with strong vegetation, (b) forms in mass on a nearly continuous basis attractive single light pink blossoms, (c) exhibits dense dark green foliage with a glossy aspect on the upper surface, (d) exhibits good tolerance to disease particularly with respect to black spot and mildew, and (e) is well suited for providing attractive ornamentation in parks and gardens.

The blooming tends to commence medium in the season during observations to date.

During observations to date, the plant has been found to be cold hardy in U.S.D.A. Hardiness Zone No. 5.

The new variety well meets the needs of the horticultural industry and can be grown to advantage in parks and gardens where ornamentation is to be provided.

The new variety can be readily distinguished from its ancestors. For instance, the 'Noacas' parental variety forms dissimilar orange to orange-red blossoms. The new variety can be distinguished from other known cultivars, as well. For example, the flowers of the new cultivar have fewer petals than the 'Korgazell' and 'Korstarnow' cultivars (non-patented in the U.S.), which exhibit approximately 9-16 petals per flower. Further, the flowers of the new cultivar have fewer petals than the 'Meibarum' cultivar (non-patented in the U.S.), which exhibit approximately 17-25 petals per flower.

The new variety has been found to undergo asexual propagation in France by a number of routes, including budding, grafting, and the use of cuttings. Asexual propagation by the above-mentioned techniques at Le Cannet des Maures, Var, France, has shown that the characteristics of the new variety are stable and are strictly transmissible by such asexual propagation from one generation to another. Accordingly, the new variety undergoes asexual propagation in a true-to-type manner.

The new variety has been named 'Meiplumty'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during July while growing on their own roots outdoors at Le Cannet des Maures, Var, France. Comparative standard color information is provided at the bottom of the photograph.

FIG. 1—illustrates a specimen of a young shoot;

FIG. 2—illustrates a specimen of a floral bud at the opening of the sepals;

FIG. 3—illustrates a specimen of a floral bud wherein the sepals are more fully open;

FIG. 4—illustrates a specimen of a floral bud at the initial opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a floral receptacle showing the arrangement of the stamens and pistils;

FIG. 9—illustrates a specimen of a floral receptacle showing the arrangement of the pistils (stamens removed);

FIG. 10—illustrates a specimen of a flowering stem;

FIG. 11—illustrates a cluster of unopened floral buds;

FIG. 12—illustrates a specimen of a leaf with three leaflets—plan view—upper surface;

FIG. 13—illustrates a specimen of a leaf with five leaflets—plan view—under surface; and FIG. 14—illustrates a specimen of a leaf with seven leaflets—plan view—upper surface.

DETAILED BOTANICAL DESCRIPTION

The chart used in the identification of the colors is that of The Royal Horticultural Society (R.H.S. Colour Chart, 1995 Edition). The description is based on the observation of one-year-old plants during May while growing outdoors on their own roots at Le Cannet des Maures, Var, France.

Class: Floribunda.

Plant:

*Growth habit*.—Bushy.

*Height*.—Approximately 50 cm on average.

*Spread*.—Approximately 70 cm on average.

Branches:

*Color*.—Young stems: near Yellow-Green Group 146D. Adult wood: near Yellow-Green Group 146C.

*Prickles*.—Small prickles commonly are absent on young and adult stems.

*Thorns*.—Configuration: slightly curved downwards on the upper surface, slightly concave on the under surface, and with an oval base. Quantity: approximately 9 on average on a stem length of 10 cm. Length: approximately 1 cm on average. Color: near Yellow-Green Group 153C amply suffused with near Greyed-Purple Group 179B. On adult stems: Quantity: approximately 3 on average on a stem length of 10 cm. Length: approximately 1.1 cm on average. Color: near Greyed-Purple Group 177B.

Leaves:

*Stipules*.—Adnate, pectinate, rather broad, approximately 1.5 cm in length on average, approximately 8 mm in width on average, near Yellow-Green Group 146B and 146C on the upper surface, and near Yellow-Green Group 146B on the under surface.

*Petioles*.—Upper surface: near Yellow-Green Group 146B in coloration. Under surface: near Yellow-Green Group 146C in coloration. Texture: non-glandular on the upper surface, and with a few small prickles on the under surface. Length: approximately 5.5-6.5 cm on average.

*Rachis*.—Upper surface: near Yellow-Green Group 146D in coloration. Under surface: near Yellow-Green Group 146B in coloration. General appearance: dense. Length: approximately 5.5-6.5 cm on average.

*Leaflets*.—Number: 3, 5 and 7 (most often). Shape: generally elliptical with a pointed tip and an obtuse base. Size: the terminal leaflets commonly are approximately 3.6 cm in length on average, and approximately 2.4 cm in width on average. Serration: slightly denticulate, small and single (as illustrated). Texture: physically firm and leathery with a glossy upper surface. Color (young foliage): Upper surface: near Green Group 137B. Under surface: near Yellow-Green Group 146B. Color (adult foliage): Upper surface: near Green Group 137B. Under surface: near Yellow-Green Group 146C.

Inflorescence:

*Number of flowers*.—Commonly approximately 5 to 10 blossoms per stem.

*Peduncle*.—Glandular, approximately 2 to 3 cm in length on average, approximately 2 mm in diameter on average, and near Green Group 138B in coloration.

*Pedicel*.—Approximately 2 to 3 cm in length on average, approximately 2 mm in diameter on average, and near Green Group 138B in coloration.

*Sepals*.—Upper surface: tomentose and near Green Group 138C in coloration. Under surface: smooth and near Green Group 138B in coloration. Shape: longish and narrow, and somewhat upright at the base. Size: approximately 2 cm in length on average, and approximately 4 mm in width at the widest point on average. Sepal extension: weak sepal extension approximately 0-2 cm in length on average.

*Buds*.—Shape: substantially conical. Size: small. Length: approximately 1.4 cm on average. Width: approximately 1 cm at the widest point on average. Color as calyx breaks: Upper surface: near White Group 155A amply suffused with near Red Group 49D at the base. Under surface: near White Group 155A with a spot of near Yellow Group 2D at the base.

*Flower*.—Shape: flattened cup-shaped. Diameter: approximately 6 cm on average. Color (in the course of opening): Upper surface: near White Group 155A amply suffused with near Red Group 49D, with a spot of near Yellow Group 2D at the base. Under surface: near White Group 155A with a spot of near Yellow Group 2D at the base. Color (open flower): Upper side: near White Group 155A with a spot of near Yellow Group 2D at the base. Under side: near White Group 155A with a spot of Yellow Group 2D at the base. Fragrance: none detected. Petal number: approximately 5 on average under normal growing conditions. Petal shape: with a substantially rounded tip and an obtuse base. Petal margin: non-serrated with a weak undulation. Petal texture: leathery and somewhat firm. Petal length: approximately 2.3 cm on average. Petal width: approximately 2 cm on average. Petal arrangement: imbricated, and without petaloids. Petal drop: good with the petals commonly detaching cleanly before drying. Stamen number: approximately 48 on average. Anthers: regularly arranged around the styles, approximately 1 mm in size on average, and near Orange Group 24B in coloration. Filaments: approximately 2 mm in length on average, and near Yellow Group 13D in coloration. Pistils: approximately 12 on average. Stigmas: approximately 1 mm in size on average, and near Yellow Group 11C in coloration. Styles: approximately 3 mm in length on average, and near Yellow-Green Group 145D in coloration. Receptacle: smooth, pitcher-shaped in longitudinal section, approximately 4 mm in length on average, approximately 3 mm in width on average at the widest point, and near Green Group 138B in coloration.

*Hip*.—Pitcher shaped, approximately 1 cm in length on average, approximately 8 mm in diameter on average, smooth in texture, and near Yellow Green 144A in coloration.

Development:

*Vegetation*.—Strong.

*Blooming*.—Medium season, very abundant and nearly continuous.

*Tolerance to diseases*.—Good, with no particular susceptibility to black spot and mildew.

The new 'Meiplumty' variety has not been observed under all possible environmental conditions to date. Accordingly, it is possible that the phenotypic expression may vary somewhat with changes in light intensity and duration, cultural practices, and other environmental conditions.

I claim:

1. A new and distinct Floribunda rose plant characterized by the following characteristics:

(a) displays a low and compact bushy growth habit with strong vegetation, (b) forms in mass on a nearly continuous basis attractive single light pink blossoms, (c) exhibits dense dark green foliage with a glossy aspect on the upper surface, (d) exhibits good tolerance to disease particularly with respect to black spot and mildew, and (e) is well suited for providing attractive ornamentation in parks and gardens;

substantially as shown and described.

* * * * *

MEIPLUMTY